(12) United States Patent
Perschbacher et al.

(10) Patent No.: US 6,522,922 B1
(45) Date of Patent: Feb. 18, 2003

(54) METHOD AND APPARATUS FOR BREAKING PACEMAKER MEDIATED BRADYCARDIA

(75) Inventors: David L. Perschbacher, Coon Rapids, MN (US); Ankur Garg, St. Paul, MN (US); James O. Gilkerson, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 166 days.

(21) Appl. No.: 09/615,546

(22) Filed: Jul. 13, 2000

(51) Int. Cl.⁷ .................................................. A61N 1/36
(52) U.S. Cl. ............................................. 607/14; 607/9
(58) Field of Search ............................ 607/9, 4, 14, 27

(56) References Cited

U.S. PATENT DOCUMENTS

| | | | | |
|---|---|---|---|---|
| 3,794,045 A | * | 2/1974 | Thaler .............................. 607/9 |
| 3,921,642 A | | 11/1975 | Preston et al. ......... 128/419 PG |
| 4,030,510 A | | 6/1977 | Bowers ................. 128/419 PG |
| 4,363,325 A | | 12/1982 | Roline et al. ......... 128/419 PG |
| 5,016,630 A | | 5/1991 | Moberg ................. 128/419 PG |
| 5,237,992 A | | 8/1993 | Poore ........................... 607/18 |
| 5,247,930 A | | 9/1993 | Begemann et al. ............ 607/11 |
| 5,282,465 A | | 2/1994 | van der Veen et al. ....... 607/17 |
| 5,284,491 A | | 2/1994 | Sutton et al. .................. 607/17 |
| 5,441,525 A | | 8/1995 | Shelton et al. ................. 607/23 |
| 5,501,701 A | | 3/1996 | Markowitz et al. ............ 607/9 |
| 5,507,782 A | * | 4/1996 | Kieval ............................ 607/9 |
| 5,531,771 A | | 7/1996 | van der Veen ................. 607/9 |
| 5,540,728 A | | 7/1996 | Shelton et al. ................. 607/23 |
| 5,676,686 A | | 10/1997 | Jensen et al. ................... 607/9 |
| 5,755,737 A | | 5/1998 | Prieve et al. ................... 607/4 |
| 5,782,886 A | | 7/1998 | Kuiper et al. ................. 607/17 |
| 5,991,659 A | | 11/1999 | de Vries et al. ................ 607/9 |

* cited by examiner

*Primary Examiner*—Angela D. Sykes
*Assistant Examiner*—Roderick Bradford
(74) *Attorney, Agent, or Firm*—Schwegman, Lundberg, Woessner & Kluth, P.A.

(57) ABSTRACT

A cardiac pacemaker programmed to pace in a demand mode with hysteresis is further programmed to recognize and correct a pacemaker mediated bradycardia. Such a pacemaker mediated bradycardia is the result of an idioventricular rhythm that occurs while hysteresis is operative and which inhibits the pacemaker from further pacing.

11 Claims, 2 Drawing Sheets

METHOD AND APPARATUS FOR BREAKING PACEMAKER MEDIATED BRADYCARDIA

FIELD OF THE INVENTION

This invention pertains to cardiac pacemakers, and in particular, to those pacemakers employing a hysteretic rate control algorithm.

Background

Cardiac pacemakers are medical devices, usually implantable, that provide electrical stimulation in the form of pacing pulses to selected chambers of the heart (i.e., the atrium and/or ventricle). As the term is used herein, a pacemaker is any cardiac rhythm management device that performs cardiac pacing, including implantable cardioverter/defibrillators having a pacing functionality. Pacemakers typically have a programmable electronic controller that causes the pacing pulses to be output in response to lapsed time intervals and sensed electrical activity (i.e., intrinsic heart beats not as a result of a pacing pulse). Implantable pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold must be delivered to the chamber.

Most pacemakers are programmed to operate in a so-called demand mode (a.k.a., synchronous mode), where a pacing pulse is delivered to a heart chamber during a cardiac cycle only when no intrinsic beat by the chamber is detected. An escape interval is defined for each paced chamber, which is the maximum time interval in which a beat must be detected before a pace will be delivered. A ventricular escape interval thus defines the minimum rate at which the pacemaker will allow the ventricle to beat, sometimes referred to as the lower rate limit or its inverse, the lower rate interval. Similarly, in a pacemaker configured to pace the atria in addition to the ventricles on a demand basis, an atrial escape interval is defined as the maximum time interval in which an atrial sense must be detected after a ventricular sense or pace before an atrial pace will be delivered. The lower rate interval in that case is the sum of the atrial escape interval and the programmed atrioventricular (AV) delay (i.e., the delay between an atrial sense or pace and a ventricular pace). If functioning properly, the pacemaker in this manner makes up for a heart's inability to pace itself at an appropriate rhythm in order to meet metabolic demand.

As pacemaker technology has developed, a number of standard operating modes have been developed which define how the device paces the heart. The modes employed for bradycardia pacing are usually described by a three-letter code developed by the Inter-Society Commission for Heart Disease where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used which implies a tracking mode), and O (for no response). A pacemaker operating in a demand mode is therefore designated with an I or a D as the third letter. Additional sensing of physiological data allows some pacemakers to change the rate at which they pace the heart in accordance with some parameter correlated to metabolic demand. Such pacemakers are called rate-adaptive and designated by a fourth letter added to the three-letter code, R.

A pacemaker operating in a demand mode may also employ hysteresis in its control algorithm to vary the escape interval. Hysteresis in this context means that if the heart starts to beat intrinsically at a rate above the lower rate limit, so that the pacemaker is not having to pace the heart, the lower rate limit is lowered to a hysteresis value. That is, the next pacing escape interval is prolonged to a hysteresis value after a spontaneous, or natural beat. The intrinsic heart rate must then fall below the hysteresis value before the pacemaker starts to pace the heart again, at which point the lower rate limit is returned to its original value. For example, the pacemaker may be programmed to pace at 60 beats per minute (bpm), but if intrinsic beats are being sensed at rates above 60 bpm, the escape interval is then lowered to a hysteresis value, e.g., 50 bpm. The advantage of hysteresis is that it enables the pacemaker to follow a natural rhythm that is just slightly below the original programmed lower rate limit (LRL) but still at a high enough rate that it is not necessary to override these natural beats with pacing. One advantage of allowing natural beats to occur to as great an extent as possible is that the longevity of the pacemaker's battery is extended due to not having to deliver as many pacing pulses. Furthermore, in a pacemaker operating in a mode that does not attempt to provide AV synchrony, such as VVI, natural beats that do provide such synchrony are physiologically better for the patient, and hysteresis provides a means of allowing such natural beats to occur as often as possible. Even in dual chamber pacemakers operating in a mode that does attempt to provide AV synchrony with atrial tracking, such as DDD or VDD, hysteresis with respect to the atrial escape interval enables increased tracking of natural atrial beats which is physiologically desirable in a chronotropically competent patient. Even in a pacemaker providing atrioventricular sequential pacing (i.e., in DDI or DVI modes) which does not track natural atrial beats, it remains desirable to maximize the number of natural beats in a patient without AV block so as to maximize the number cardiac cycles where the heart is permitted to beat with its own natural AV synchrony.

SUMMARY OF THE INVENTION

A problem that arises with a conventional demand mode pacemaker that employs hysteresis with respect to an atrial escape interval, however, is a pacemaker mediated bradycardia which may be induced when an idioventricular rhythm occurs. In that situation, although the heart is beating abnormally and with no atrial contractions, the pacemaker does not intervene and delivers no pacing.

It is a primary objective of the present invention to provide a way for a pacemaker employing a hysteretic control algorithm to break the pacemaker mediated bradycardia induced by an idioventricular rhythm. In such a pacemaker, atrial and ventricular senses corresponding to depolarizations are detected with atrial and ventricular sensing channels, and pacing is delivered to the ventricles, as well as possibly the atria, according to a programmed bradycardia pacing mode. The pacemaker employs an atrial escape interval after which an atrial pace is delivered (according to a programmed bradycardia pacing mode) following a ventricular pace or sense if no ventricular or atrial sense is detected within the escape interval. The control algorithm exhibits hysteresis by which the escape interval is lengthened to a hysteretic value in response to an atrial sense within the original escape interval. While the hysteretic escape interval is operative, an idioventricular rhythm at a rate faster than the hysteretic limit rate would inhibit a conventional pacemaker from delivering any further pacing. In accordance with the present invention, the pacemaker is configured to return the escape interval to the non-hysteretic programmed value (which may be a sensor indicated rate in the case of a rate-adaptive pacemaker) upon detecting a programmable number of ventricular senses not preceded by atrial senses. In this manner, the pacemaker mediated bradycardia induced by the idioventricular rhythm is broken and pacing is resumed.

DETAILED DESCRIPTION OF THE INVENTION

One of the most common indications for artificial pacemaker implantation is atrio-ventricular (AV) block, where the conduction pathways from the atria to the ventricles is interrupted. Such a block may be to due to disease in the AV node or in the conducting systems below the node. In such cases, where impulses from the normal pacemaker of the heart, the sino-atrial (SA) node are prevented from reaching the ventricles, tissue below the block with rhythmic discharge properties then becomes the pacemaker for the ventricles, a condition termed an idioventricular rhythm. In patients with infranodal AV block, due to disease in the bundle of His for example, the ventricular pacemaker becomes the tissue distal to the block with the fastest discharge rate, which is generally well below the spontaneous discharge rate of the SA node. In patients with AV nodal block, however, the remaining nodal tissue becomes the pacemaker, and AV nodal tissue spontaneously discharges at a considerably faster rate than the Purkinje fibers making up the bundle of His. In either case, however, the low ventricular rate coupled with the lack of AV synchrony may result in some degree of cerebral ischemia, causing dizziness and fainting (Stokes-Adams syndrome).

Figure 1:
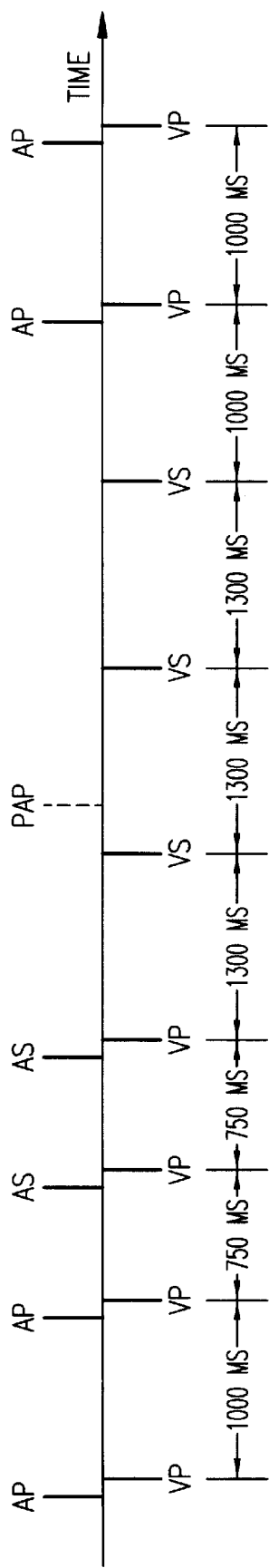
FIG. 1 is a diagram of paces and senses in a dual-chamber pacemaker with a hysteretic control algorithm showing pacemaker mediated bradycardia.

In patients having a pacemaker that paces in a mode using hysteresis, an idioventricular rhythm occurring while a hysteretic escape interval is operative can inhibit the pacemaker from pacing, leaving the patient to suffer the deleterious effects noted above. FIG. 1 illustrates the operation of a dual-chamber DDD pacemaker in this situation, showing a series of pace and sense events. In this example, the lower rate interval LRI is programmed to be 1000 ms (corresponding to a lower rate limit LRL of 60 bpm) with a fixed atrio-ventricular delay interval AVI of 150 ms. The atrial escape interval AEI is then derived as the LRL minus the AVI, or 850 ms. The hysteresis offset is set at 20 bpm (corresponding to a hysteresis interval offset of 500 ms) such that when a natural atrial beat is detected (i.e., an atrial sense), the LRL and AEI are decreased to hysteretic values of 1500 and 1350 ms, respectively.

In FIG. 1, the first and second beats each consist of an atrial pace AP followed by a ventricular pace VP at the end of the AV delay interval. The two beats are separated by the programmed lower rate interval of 1000 ms, with an atrial pace occurring after the ventricular pace at the atrial escape interval of 850 ms. At the third beat, an atrial sense AS is detected, indicating a natural atrial beat occurring within the atrial escape interval. Here, the atrial beat occurs 600 ms after the previous ventricular pace. It is assumed in this example that the patient has at least some degree of AV block, so that the atrial sense does not cause a ventricular contraction, and a ventricular pace is delivered 150 ms after the atrial sense. When the atrial sense is detected, the hysteretic control algorithm raises the LRI and AEI to their hysteretic values, so that the atrium will be allowed to beat on its own and trigger ventricular pacing pulses to a rate as low as 40 bpm. The fourth beat is another AS/VP cycle occurring well within the hysteretic atrial escape interval. The fifth beat, however, is a ventricular beat resulting from the spontaneous discharge of AV nodal or infranodal pacemaker tissue that occurs 1300 ms after the previous ventricular pace (i.e., an idioventricular rhythm). The pacemaker thus detects a ventricular sense within the hysteretic atrial escape interval of 1350 ms. Both the atrial and ventricular pacing channels of a dual-chamber pacemaker must be programmed to be inhibited by a ventricular sense in any pacing mode, because delivering a pace to either the atria or the ventricles at that time would be pointless, as well as possibly proarrhythmic. Even though no atrial sense has been detected within the hysteretic atrial escape interval at the time of the fifth beat, therefore, no atrial pace is delivered. The figure shows a pseudo atrial pace PAP that indicates where an atrial pace would have occurred were it not for the ventricular sense. If the ventricular rhythm is at a rate high enough such that ventricular senses continue to occur within the hysteretic atrial escape interval, the pacemaker is inhibited from further pacing. A pacemaker mediated bradycardia is thus induced that the pacemaker's normal programming is unable to stop.

In accordance with the invention, the pacemaker is programmed so that detection of a programmable number of ventricular senses not preceded by an atrial sense or pace causes hysteresis to be discontinued. FIG. 1 shows that after the programmed number of ventricular senses are detected (which in this case is three), a pacemaker mediated bradycardia PMB is detected by the device, and the atrial escape interval is returned to its pre-hysteretic programmed value of 850 ms. (In the case of a rate-adaptive pacemaker, where the escape intervals are adjusted in accordance with data from a physiological sensor, a hysteretic escape interval is returned to the sensor-indicated rate.) An atrial pace AP is thus shown as being delivered 850 ms after the last idioventricular beat, which is followed by a ventricular pace VP. The pacemaker then continues with AP/VP cycles at the programmed lower rate limit to terminate the pacemaker mediated bradycardia.

Figure 2:
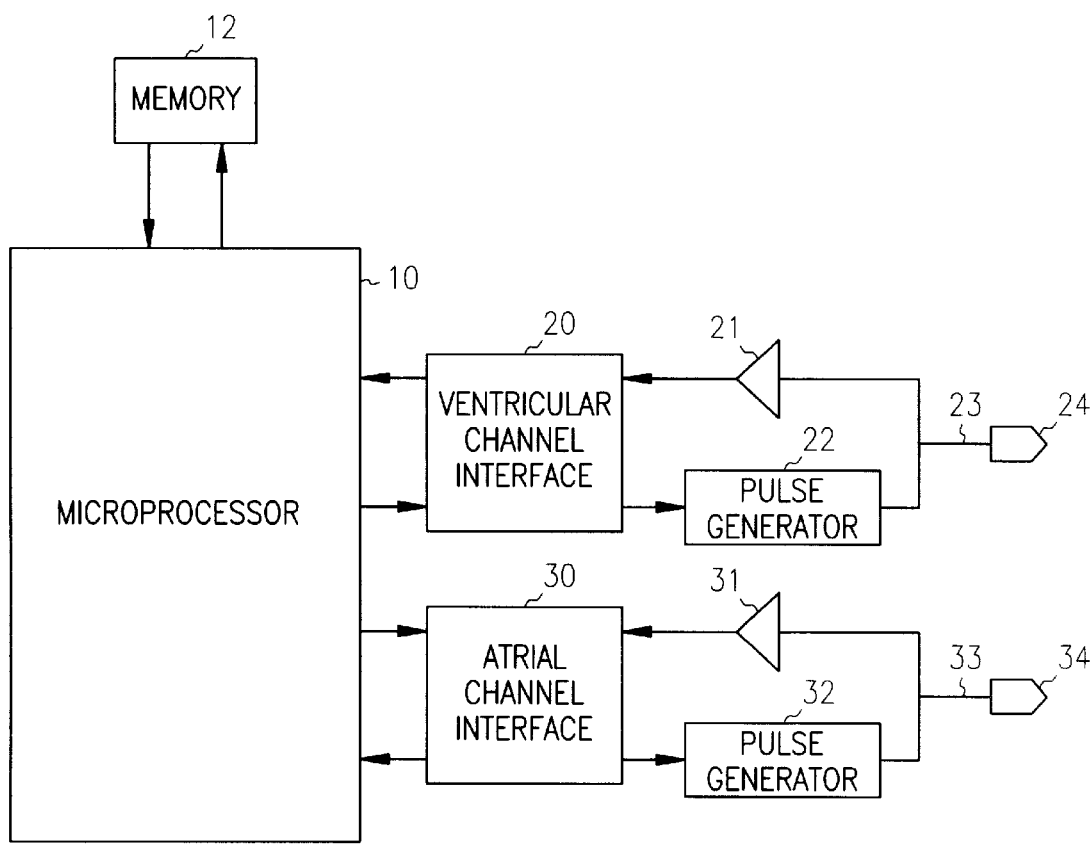
FIG. 2 is a block diagram of an exemplary pacemaker in which may be incorporated the present invention.

FIG. 2 shows a system diagram of a microprocessor-based dual-chamber pacemaker. A microprocessor 10 communicates with a memory 12 via a bidirectional data bus. The memory 12 typically comprises a ROM for program storage and a RAM for data storage. The pacemaker has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The channel interfaces 20 and 30 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

In one embodiment, the pacemaker is programmed to operate in a DDD mode such that an atrial pace is delivered following a ventricular sense or pace if an atrial or ventricular sense is not detected within an atrial escape interval following the ventricular sense or pace, and a ventricular pace is delivered following an atrial sense or pace if a ventricular sense is not detected within a specified atrio-ventricular interval following the atrial sense or pace. The atrial escape interval is set at a programmed value but is raised to a hysteresis value following an atrial sense. The atrial escape interval remains at the hysteresis value until an atrial pace is delivered or a specified number of ventricular senses are detected not immediately preceded by an atrial sense, whereupon the interval is returned to the programmed value.

In another embodiment, the pacemaker is programmed to operate in a VDD mode such that a ventricular pace is delivered following an atrial sense if a ventricular sense is not detected within a specified atrio-ventricular interval following the atrial sense, or if a ventricular sense is not detected within a ventricular escape interval following a ventricular sense or pace. The atrial escape interval is initially set at a programmed value but is raised to a hysteresis value following an atrial sense. The atrial escape interval remains at the hysteresis value until a specified number of ventricular senses are detected that are not immediately preceded by an atrial sense, whereupon the interval is returned to the programmed value.

In another embodiment, the pacemaker is programmed to operate in a VDD mode such that a ventricular pace is delivered following an atrial sense if a ventricular sense is not detected within a specified atrio-ventricular interval following the atrial sense, or if a ventricular sense is not detected within a ventricular escape interval following a ventricular sense or pace. The atrial escape interval is initially set at a programmed value but is raised to a hysteresis value following an atrial sense. The atrial escape interval remains at the hysteresis value until a specified number of ventricular senses are detected that are not immediately preceded by an atrial sense, whereupon the interval is returned to the programmed value.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac pacemaker, comprising:
   detecting atrial and ventricular senses corresponding to depolarizations with atrial and ventricular sensing channels;
   delivering a pace to a chamber of the heart in a demand pacing mode defined by an escape interval; and,
   wherein the escape interval is set at a programmed value but is raised to a hysteresis value following an atrial sense, the escape interval remaining at the hysteresis value until an atrial pace is delivered or a specified number of ventricular senses are detected not immediately preceded by an atrial sense, whereupon the interval is returned to the programmed value.

2. The method of claim 1 wherein the escape interval is an atrial escape interval and further comprising:
   delivering an atrial pace following a ventricular sense or pace if an atrial or ventricular sense is not detected within the atrial escape interval following the ventricular sense or pace;
   delivering a ventricular pace following an atrial sense or pace if a ventricular sense is not detected within a specified atrio-ventricular interval following the atrial sense or pace; and,
   wherein the atrial escape interval is set at a programmed value but is raised to a hysteresis value following an atrial sense, the atrial escape interval remaining at the hysteresis value until an atrial pace is delivered or a specified number of ventricular senses are detected not immediately preceded by an atrial sense, whereupon the interval is returned to the programmed value.

3. The method of claim 1 wherein the escape interval is an atrial escape interval and further comprising:
   delivering an atrial pace following a ventricular pace or sense if no ventricular or atrial sense is detected within the atrial escape interval;
   wherein the atrial escape interval is set at a programmed value but is raised to a hysteresis value following an atrial sense, the atrial escape interval remaining at the hysteresis value until an atrial pace is delivered or a specified number of ventricular senses are detected not immediately preceded by an atrial sense, whereupon the interval is returned to the programmed value.

4. The method of claim 1 wherein the escape interval is an atrial escape interval and further comprising:
   delivering an atrial pace if an atrial or ventricular sense is not detected within the atrial escape interval following a ventricular sense or pace;
   delivering a ventricular pace if a ventricular sense is not detected within a ventricular escape interval following a ventricular sense or pace; and,
   wherein the atrial and ventricular escape intervals are set at programmed values but are raised to hysteresis values following an atrial sense, the escape intervals remaining at the hysteresis values until an atrial pace is delivered or a specified number of ventricular senses are detected not immediately preceded by an atrial sense, whereupon the intervals are returned to the programmed values.

5. A processor-executable medium containing instructions for performing the method set forth in claim 2.

6. A processor-executable medium containing instructions for performing the method set forth in claim 3.

7. A processor-executable medium containing instructions for performing the method set forth in claim 4.

8. A cardiac pacemaker, comprising:
   atrial and ventricular sensing channels, each such channel comprising an electrode for disposing near a chamber of the heart and a sense amplifier for detecting sense signals;
   a ventricular pacing channel comprising a pulse generator for outputting ventricular pacing pulses;
   an atrial pacing channel comprising a pulse generator for outputting atrial pacing pulses;

a controller for controlling the operation of the pulse generators;

wherein the controller is programmed to:

deliver a pace to a chamber of the heart in a demand pacing mode defined by an escape interval; and, wherein the escape interval is set at a programmed value but is raised to a hysteresis value following an atrial sense, the escape interval remaining at the hysteresis value until an atrial pace is delivered or a specified number of ventricular senses are detected not immediately preceded by an atrial sense, whereupon the interval is returned to the programmed value.

9. The pacemaker of claim 8 wherein the escape interval is an atrial escape interval and the controller is programmed to:

deliver an atrial pace following a ventricular sense or pace if an atrial or ventricular sense is not detected within the atrial escape interval following the ventricular sense or pace;

deliver a ventricular pace following an atrial sense or pace if a ventricular sense is not detected within a specified atrio-ventricular interval following the atrial sense or pace; and, wherein the atrial escape interval is set at a programmed value but is raised to a hysteresis value following an atrial sense, the atrial escape interval remaining at the hysteresis value until an atrial pace is delivered or a specified number of ventricular senses are detected not immediately preceded by an atrial sense, whereupon the interval is returned to the programmed value.

10. The pacemaker of claim 8 wherein the escape interval is an atrial escape interval and the controller is programmed to:

deliver an atrial pace following a ventricular pace or sense if no ventricular or atrial sense is detected within the atrial escape interval; and, wherein the atrial escape interval is set at a programmed value but is raised to a hysteresis value following an atrial sense, the atrial escape interval remaining at the hysteresis value until an atrial pace is delivered or a specified number of ventricular senses are detected not immediately preceded by an atrial sense, whereupon the interval is returned to the programmed value.

11. The pacemaker of claim 8 wherein the escape interval is an atrial escape interval and the controller is programmed to:

deliver an atrial pace if an atrial or ventricular sense is not detected within the atrial escape interval following a ventricular sense or pace;

deliver a ventricular pace if a ventricular sense is not detected within a ventricular escape interval following a ventricular sense or pace; and, wherein the atrial and ventricular escape intervals are set at programmed values but are raised to hysteresis values following an atrial sense, the escape intervals remaining at the hysteresis values until an atrial pace is delivered or a specified number of ventricular senses are detected not immediately preceded by an atrial sense, whereupon the intervals are returned to the programmed values.

* * * * *

UNITED STATES PATENT AND TRADEMARK OFFICE
CERTIFICATE OF CORRECTION

| | |
|---|---|
| PATENT NO. | : 6,522,922 B1 |
| APPLICATION NO. | : 09/615546 |
| DATED | : February 18, 2003 |
| INVENTOR(S) | : David L. Perschbacher, Ankur Garg and James O. Gilkerson |

It is certified that error appears in the above-identified patent and that said Letters Patent is hereby corrected as shown below:

In column 5, lines 25-37, delete the following paragraph:

"In another embodiment, the pacemaker is programmed to operate in a VDD mode such that a ventricular pace is delivered following an atrial sense if a ventricular sense is not detected within a specified atrio-ventricular interval following the atrial sense, or if a ventricular sense is not detected within a ventricular escape interval following a ventricular sense or pace. The atrial escape interval is initially set at a programmed value but is raised to a hysteresis value following an atrial sense. The atrial escape interval remains at the hysteresis value until a specified number of ventricular senses are detected that are not immediately preceded by an atrial sense, whereupon the interval is returned to the programmed value."

In column 5, lines 38-50, delete the following paragraph:

"In another embodiment, the pacemaker is programmed to operate in a VDD mode such that a ventricular pace is delivered following an atrial sense if a ventricular sense is not detected within a specified atrio-ventricular interval following the atrial sense, or if a ventricular sense is not detected within a ventricular escape interval following a ventricular sense or pace. The atrial escape interval is initially set at a programmed value but is raised to a hysteresis value following an atrial sense. The atrial escape interval remains at the hysteresis value until a specified number of ventricular senses are detected that are not immediately preceded by an atrial sense, whereupon the interval is returned to the programmed value."

and insert the following paragraph:

--In another embodiment, the pacemaker is programmed to operate in a DDI mode such an atrial pace is delivered if an atrial or ventricular sense is not detected within an atrial escape interval following a ventricular sense or pace, and a ventricular pace is delivered if a ventricular sense is not detected within a ventricular escape interval following a ventricular sense or pace. The atrial and ventricular escape intervals are initially set at programmed values but are raised to hysteresis values following an atrial sense. The escape intervals remain at the hysteresis values until an atrial pace is delivered or a specified number of ventricular senses are detected not immediately preceded by an atrial sense, whereupon the intervals are returned to the programmed values.-- therefor.

UNITED STATES PATENT AND TRADEMARK OFFICE
CERTIFICATE OF CORRECTION

PATENT NO. : 6,522,922 B1
APPLICATION NO. : 09/615546
DATED : February 18, 2003
INVENTOR(S) : David L. Perschbacher, Ankur Garg and James O. Gilkerson It is certified that error appears in the above-identified patent and that said Letters Patent is hereby corrected as shown below:

In column 6, line 28, in claim 3, insert --and,-- after "interval;".

Signed and Sealed this

Fourteenth Day of July, 2009

JOHN DOLL
*Acting Director of the United States Patent and Trademark Office*